United States Patent [19]
Singh et al.

[11] Patent Number: 5,858,371
[45] Date of Patent: Jan. 12, 1999

[54] PHARMACEUTICAL COMPOSITION FOR THE CONTROL AND TREATMENT OF ANORECTAL AND COLONIC DISEASES

[75] Inventors: Amarjit Singh, Chandigarh; Rajesh Jain, New Delhi; Anil Kumar Singla, Chandigarh, all of India

[73] Assignees: Panacea Biotech Limited, New Delhi; University Institute of Pharmaceutical Sciences, Punjab, both of India

[21] Appl. No.: 837,564

[22] Filed: Apr. 21, 1997

[30] Foreign Application Priority Data

Feb. 5, 1997 [IN] India ................... 316/Del/97

[51] Int. Cl.⁶ .................... A61K 35/78; A61K 39/385
[52] U.S. Cl. .................... 424/195.1; 424/642; 514/27; 514/456; 514/882
[58] Field of Search .................. 514/27, 456; 424/195.1

[56] References Cited

U.S. PATENT DOCUMENTS

| | | |
|---|---|---|
| 4,160,148 | 7/1979 | Jenkins . |
| 4,508,728 | 4/1985 | Nagai et al. . |
| 4,518,583 | 5/1985 | Gallina . |
| 4,613,498 | 9/1986 | Crosby . |
| 4,621,635 | 11/1986 | Ali . |
| 4,626,433 | 12/1986 | Gros . |
| 4,797,392 | 1/1989 | Chernomorsky . |
| 5,166,132 | 11/1992 | Gordon . |
| 5,219,880 | 6/1993 | Thornfeldt . |
| 5,234,914 | 8/1993 | Gallina . |
| 5,562,906 | 10/1996 | Terry et al. . |
| 5,591,436 | 1/1997 | Pruthi . |

FOREIGN PATENT DOCUMENTS

| | | |
|---|---|---|
| 0091405 | 10/1983 | European Pat. Off. . |
| 0225832 | 6/1987 | European Pat. Off. . |
| 0095142 | 10/1988 | European Pat. Off. . |
| 0116688 | 5/1989 | European Pat. Off. . |
| 0513442 | 11/1992 | European Pat. Off. . |
| WO 9527491A1 | 6/1995 | France . |
| WO 88/03398 | 5/1988 | WIPO . |
| WO 96/32081 | 10/1996 | WIPO . |

OTHER PUBLICATIONS

Bennett et al., "Inhibitory effects of natural flavonoids on secretion from mast cells and neutrophils" *Arzneim. Forsch*, (1981)31(3):433–437.
Busse et al., "Flavonoid modulation of human neutrophil function" *J. Allergy Clin. Pharmacol.* (1984)73:801–809.
Havsteen, "Flavonoids, a class of natural products of high pharmacological potency" *Biochem. Pharmacol.* (1983)32:1141–1148.
Kalashnikov et al., "Antiphlogistic activity of several flavonoids" *Chem. Abstract* (1976) 84:39 (Abstract No. 99346).
Parmar et al., "Anti–inflammatory activity of gossypin a bioflavonoid isolated from *hibiscus vitiflolius* linn" *Ind. J. Pharmacol.* (1978)10(4):277–293.
Roshchin et al., "Antiinflammatory activit of some flavonoids" *Chem. Abstract*(1975) 83:38 (Abstract No. 37683).
Schrier et al., "The topical anti–inflammatory effects of a topical preparation of meclofenamic acid on carrageenan–induced footpad swelling in mice" *J. Pharm. Pharmacol.*(1987)39:57–59.
Sekiya et al., "Selective inhibition of platelet lipoxygenase by baicalein" *Biochem. Biophys. Res. Commun.*(1982)105(3):1090–1095.
Singla et al., "Anti–inflammatory studies on *euphorbia prostrata*" *J. Ethnopharmacol.*(1989)27:55–61.
Singla et al., "Topical antiinflammatory effects of *euphorbia prostrata* on carrageenan–induced footpad oedema in mice" *J. Ethnopharmacol.*(1990)29:291–294.
Agarwal, O.P., "The anti–inflammatory action of nepitrin, a flavonoid" *Agents and Actions* (1982)12(3):298–302.
Gabor, M.H., "Anti–inflammatory substances of plant origin" *Handbood of Experimental Pharmacology:Antiinflammatory Drugs*, G.V.R. Born et al. (Eds.) Spring NY (1979) vol. 50/II, Ch. 39, pp. 698–739.
Kalashnikova et al., "Anti–inflammatory activity of some flavonoids" *Aktual. Vopr. Farm.* (1974)2:353. (English translation included).
Roschin et al., "Anti–inflammatory activity of some flavonoids" *Vopr. Farm. Dal'nem Vostoke* (1973)1:134–5 (Russ.). [*Chemical Abstracts*, (1975) vol. 83, #37683q — Abstract only].
Makhkamova et al., Farm. Zh(Kiev), 27(1), 57–9 (Abstract), 1972.
Polinicencu et al, Intrep. De Medicamente (Romania) (Abstract), 1983.
Buckshee et al. Int. J. Gynecol. Ob Stet 52(2), 145–51 (Abstract), 1997.

*Primary Examiner*—Leonard Schenkman
*Attorney, Agent, or Firm*—Morrison and Foerster LLP

[57] ABSTRACT

A Novel composition and a method for treating anorectal diseases including hemorrhoids and colonic diseases with long term effectiveness and low prolapse rates is disclosed. The compositions are water soluble and can be uniformly applied in the affected region. The composition comprises Flavonoidal constituents which possess anti-inflammatory properties.

31 Claims, No Drawings

PHARMACEUTICAL COMPOSITION FOR THE CONTROL AND TREATMENT OF ANORECTAL AND COLONIC DISEASES

TECHNICAL FIELD

The invention relates to a normal compositions of ingredients useful for the treatment of anorectal and colonic diseases (including hemorrhoids). The novel composition possess properties to control inflammation, prevent capillary bleeding and fragility in mammals particularly human beings.

BACKGROUND OF THE INVENTION

Anorectal and colonic diseases are usually characterised by inflammation of the infected region. Other common symptoms are those associated with inflammation, like heat, itching, redness, pain and swelling. A common characteristic of such anorectal and colonic diseases is the appearance of fissures, cracks, fistulas and abscesses.

Among the various anorectal and colonic diseases, hemorrhoids occupy a prominent position and have been the subject of numerous clinical studies. Hemorrhoidal disease is characterised by bleeding, without any pain. Fresh blood spots occur immediately, on defecation. However, pain occurs when the hemorrhoids are secondarily infected, or complicated by thrombosis and anal fissures. Hemorrhoids is characterised by episodes of acute hemorrhoid attacks, with bleeding, pain and prolapse of hemorrhoidal mass.

Thus, an effective treatment of acute hemorrhoidal attacks should not only provide relief as early as 2–3 days, after initiation of the treatment, but also reduce the recurrence of such attacks.

There exist several procedures for the treatment of hemorrhoids. Patents have been granted in respect of surgical dressings (WO 8803398) and surgical devices (European patent No. 0095142). A patent, (U.S. Pat. No. 4,621,635) has been granted for the use of lasers in the treatment of hemorrhoids. The techniques of cryopharmacotherapy and electrochemical techniques for treatment of hemorrhoids have also been patented vide European patent No. 0091405 and European Patent No. 0116688, respectively. However, the biggest drawbacks of the above, are the involvement of medical experts beyond mere prescription of medicines and probable hospitalisation. Also, some of them are physically and/or psychologically unpleasant in application.

Several patents (U.S Pat. Nos. 4,160,148, 4,508,728, 4,797,392, 4,518,583 and 5,234,914) have been granted in the United States of America in respect of compositions containing certain wound healing agents to provide symptomatic relief, by promoting tissue repair, reducing inflammation and encouraging wound healing. Some of them like U.S. Pat. Nos. 4,518,583 and 5,234,914 contain antimicrobial agents. These compositions, however, only relieve symptoms associated with inflammation, like heat, itching, redness, pain and swelling.

A number of compositions for the treatment of anorectal diseases (including hemorrhoids) are based on the anaesthetic and vasoconstrictive properties of the constituents, but these provide only temporary symptomatic relief.

Patents in the United States of America (U.S. Pat. Nos. 4,613,498, 4,626,433, 5,166,132, 5,219,880, 5,234,914 and 4,797,392) and Europe (European Patents Nos. 0225832 and 0513442) have been granted in respect of compositions with varying constituents, for topical application in the form of suitable and acceptable pharmaceutical carriers, such as salts, salves, ointments etc., with organic, inorganic and biological active agents. However, these compositions provide only temporary relief and are limited to local application and cannot be used for systemic use or oral administration.

A topical treatment for hemorrhoidal pain and for spasms of the sphintcters and muscles located in the GI tract is disclosed in a granted patent (U.S. Pat. No. 595,753) which includes amino acid L-arginine in a pharmaceutically acceptable carrier. Another U.S. Pat. No. (5,591,436) has been granted for a composition for dietary supplement for the treatment of hemorrhoids. The composition comprisis 60% to 95% Indian Barberry by weight; 4.8% to 38% Nagkesar by weight; and 0.2% to 2% Margosa tree leaves by weight.

Another U.S. Pat. No. (5,562,906) discloses the use of bark or berries of the species *Xanthoxylum clavaherculis* L and *Xanthoxylum americanum* Hill, both of the yellow wood tree family, both containing the compound Xanthoxylum are employed for the treatment of hemorrhoids and other membrane and capillary disorders of the veins and arteries. Improved strength and flexibility of the veins, arteries and their constituent structures is obtained.

There is available in the market, pharmaceutical compositions containing diosmin and a combination of diosmin and hesperidin for the treatment of hemorrhoids. However, the concentration of diosmin and hesperidin in such compositions is much higher than the concentrations of flavonoids of the present invention. Besides such diosmin and hesperidin are obtained from synthetic sources.

The inventors have researched, and as a result of the expenditure of time and mental faculties have found that the flavonoid composition of the present invention exhibits surprisingly significant enhanced pharmacological and therapeutic response at much lower dosage levels in comparison to existing compositions employing flavonoids.

The present invention provides a Pharmaceutical composition which is safe and painless and has long term effectiveness.

SUMMARY OF THE INVENTION

A composition and a method for treating anorectal diseases including hemorrhoids and colonic diseases with long term effectiveness and low prolapse rates. The treatment includes applying to the hemorrhoids and anorectal tissues an effective amount of composition including a pharmaceutically acceptable carrier and a mixture of flavonoids. The treatment also includes administration by oral route and/or parenteral route an effective amount of composition including a pharmaceutically acceptable carrier and mixture of flavonoids

DETAILED DESCRIPTION OF THE PREFERRED EMBODIMENTS

This invention provides compositions which are water soluble and can be uniformly distributed in the affected region. It reduces inflammation, and soothes the feeling of itching and burning associated with it. The invention also provides relief from pain, which characterises hemorrhoids. Growth of microorganisms is also prevented by the composition when administered in any manner. The invention is useful in the treatment of lesions, other than hemorrhoids in the anorectal area and can be formulated in several types of Dosage Forms. There are no side effects from the use of the composition in human beings. Further, the treatment is not physically or psychologically unpleasant in its application. The plant *Euphorbia prostrata* (Family: Euphorbiaceae) was identified as being relevant in the study of anorectal and colonic diseases, including hemorrhoids. *Euphorbia prostrata* is well known to the Indian traditional medicine in the use of treatment for asthma, bloody dysentery and sores. (Five new compounds were discovered and identified by the inventors in *Euphorbia prostrata* (FIG. 1) namely luteolin, 6-methoxy-quercetin-glycoside, Querceitin, and glycosides of luteolin and apigenin. *Euphorbia prostrata* contains 1–2.5% of total flavonoids. Out of which apigenin glycoside is 0.8–1.4%, luteolin glycoside is 0.2–0.5%, 6-methoxy-quercetin-glycoside is 0.2%, quercetin and luteolin is 0.1%.

These flavonoidal constituents are reported to have anti-inflammatory properties. These compounds were extracted from *Euphorbia prostrata* for testing and combined in a proportion, which is new and has not been reported before. The compounds in such proportion were standardised to pharmaceutically acceptable specifications in order to ensure reproducibility from batch to batch. The result is the standardised extract of *Euphorbia prostrata*, which is the main active agent in the improved anorectal composition. Another unique feature of this extract of *Euphorbia prostrata* is, that it is prepared in such a manner that the resulting composition is water soluble. Pharmaceutical dosage carriers used in the present invention are capsules, tablets, ointments, creams, gels, foams, aerosols, sprays, and the like.

Other plants containing apigenin glycosides and luteolin glycosides are *Ixora arborea* (Rubiaceae), *Bommervia hispida* (Pteridaceae), *Adenocalymma alliaceum* (Bignomiaceae), *Thalictrum thunbergii* (Renunculaceae), *Perilla frutescens* (Labiateae), *Matricaria chamomilla* (Compositae), *Thymus membranaceous* (Labiateae), *Digitalis lanata* (Scrophulariaceae), *Cuminum cyminum* (Umbelliferae), *Petroselinum, Euphorbia minuta, E.Serpeus-microfolia, Egranulata. Chrysenthemum indicum* and *Matricaria chamomilla* (Compositae) contain both apigenin and luteolin.

Glycosides of quercetin has been reported from different species of Euphorbia (*E. verrueosa, E platiphyllos, E.discolor, E. dulcis, E. helioscopia, E. thymifolia* etc.).

The pharmaceutical composition containing the standardised extract of *Euphorbia prostrata* as the active ingredient contains 35–62% flavonoids. Out of which apigenin glycoside is 30–45%, luteolin glycoside is 3–9%, 6-methoxy quercetin glycoside is 1–6%, quercetin and luteolin is 1–2%. The Extract also contains tannins (5%), resins and gums (10–15%), besides pigments, sterols, triterpenoids etc.

The pharmaceutical composition of the present invention may also contain the active agents from other plants and/or from different pharmacological groups such as local anesthetics, vasoconstrictors, protectants, counterirritants, astringents, keratolytics and anticholinergics.

Preferably, it would be beneficial to include other wound healing and antimicrobial agents which will result in the improvement of the effectiveness of the composition.

The local anesthetics and/or their salts, include but are not limited to such as benzocaine, diperodon, pramoxine, camphor, dibucaine, phenol, tetrtacaine, lignocaine and phenacaine. The amount of such anesthetics could vary between 0.25% and 25% by weight.

The vasoconstrictors include but are not limited to ephedrine, phenylephrine, phenylephrine and/or their salts. The amount of such vasoconstrictors may vary between 0.005% and 1.5% by weight.

The protectants include but are not limited to aluminum hydroxide gel, calamine, cocoa butter, cod or shark liver oil, glycerin in aqueous solution, kaolin, lanolin, mineral oil, starch, white petrolatum, wool alcohol, zinc oxide, vegetable or castor oil, polyethylene glycol and propylene glycol. The amount of such protectants may vary between 5.0% and 88.0% by weight.

The counterirritant includes but is not limited to menthol in aqueous solution. The amount of such counterirritant may vary between 0.25–2.5% by weight.

The astringents include but are not limited to calamine, zinc oxide, hamamelis water, bismuthresorcinol compound, bismuth subgallate, peruvian balsam, aluminium chlorhydroxy allantoinate, tannic acid and tannins. The amount of such astringents may vary between 0.2% to 60.0% by weight. The tannins additionally may be derived from plants such as *Butea monosperma* (Family: Leguminosae) *Butea parviflora* and *Butea frondoza*.

The wound healing agents include but are not limited to vitamin A and vitamin D in an amount by weight of between 0.005% to 0.04%. Also peruvian balsam can be included by weight in an amount of between about 0.5% to 2.5%. Also cod liver oil can be included by weight in an amount between 1.0% to 6.0%. Also live yeast cell derivative can be included in an amount of between 2–50,000 units per gram.

The antimicrobial agents, include but are not limited to benzethonium chloride, benzalkonium chloride, boric acid, 8-quinolinol benzoate, secondary amyltricresols, cetylpyridinium chloride, phenol, menthol, chlorothymol, camphor and 8-hydroxyquinoline sulfate. The amount of such antimicrobial agents vary between 0.02% and 40.0% by weight.

The keratolytics include but are not limited to aluminium chlorhydroxy allantoinate and resorcinol. The amount of such keratolytics may vary between 0.2% and 3.5% by weight.

The anticholinergics include but are not limited to atropine or other solanaceous type alkaloids, either alone or in combination. The amount of such anticholinergics may vary between 0.02% and 0.1% by weight.

The pharmaceutical compositions of the present invention can be dissolved or dispersed in an appropriate base, which can be suppositories, ointments, foams, sprays, medicated pads, capsules and tablets.

The capsules contain 5–50mg of the standardized extract of *Euphorbia prostrate*, preferably 9–15mg along with pharmaceutical excipients. Similarly, tablets may be prepared by dispersing 5–50mg of the standardized extract of *Euphorbia prostrata*, preferably 9–15 mg alongwith pharmaceutical excipients. The tablets may be coated or uncoated.

The ointment may contain 0.1–10% w/w of the standardized extract of *Euphorbia prostrata*, preferably 0.2–5%. The capsule may be taken, subject to a maximum of 100 mg per day, alongwith topical application containing the same extract, as and when required.

The granules in ready dispersible and effervescent form may be prepared by using excipients sucrose, mannitol, sodium bicarbonate, citric acid, sodium chloride etc., The cream may be prepared by emulsifying the aqueous phase, containing the active agent (0.1–10%, w/w preferably 0.2–5%), along with a suitable oleagenous phase, such that it results in a water soluble cream.

Other alternatives can be prepared by formulating the Standardized Extract in 0.1–10% w/w as hydrophilic ointment (USP) absorption base, or water soluble bases, such as PEG ointment, (USNF) or as water absorbing bases such as hydrophilic petrolatum USP, lanolin USP or in hydrocarbon bases, such as white petrolatum USP.

The suppository compositions may contain either hydrobhobic or hydrophilic base and can include cocoa butter, glycerinated gelatin, hydrogenated vegetable oils, mixtures of polyethylene glycols of various molecular weights, polyoxyethylene sorbitan fatty acid esters and polyethylene stearates, polyvinyl alcohol, polyvinyl pyrrolidone, polyacrylamide, chemically modified starch or a combination of these materials.

The foam and spray bases may contain one or more of aqueous and nonaqueous solvents, propellants, surfectants, suspending and stabilising agents.

The medicated pads may contain one or more of the following: Water, glycerin, propylene glycol, alcohol and Hamamelis water.

EVALUATION OF PHARMACOLOGICAL ACTIVITY OF THE STANDARDIZED EXTRACT

ORAL ANTI INFLAMMATORY ACTIVITY (AIA):

Studies with the standardized extract of *Euphorbia prostrata*, when administered orally showed an inhibition of both carrageenan-induced oedema at t=180 min (b=0.019, r=0.965, p<0.001) with $ED_{50}$ value of 5.98 mg/kg (95% c. I=11.71–23.68) and histamine-induced oedema (b=0.019, r=0.860. p<0.00l) with $ED_{50}$ value 16.37 mg/kg (95% CL=0.01–32.73).

Carrageenan-induced oedema is a biphasic event, the early hypermia being due to the release of histamine and serotonin and the delayed oedema due to the release of bradykinin and prostaglandins. The findings shown in Table 1, indicate that the orally administered standardized extract (200 mg/kg) is effective against both phases of inflammation, inhibiting 76% of oedema and equivalent to 74% inhibition by 1 mg/kg of indomethacin (i. p.).

The results have been further supported by the experiments carried out in histamine and bradykinin induced oedema models. The data shown in Table 2 indicates 77% and 56% inhibition of oedema at +60 and +120 min in the histamine-induced oedema model, while in the bradykinin-induced model the effect was significant (p<0.001) only at +180 min.

TABLE 2

Effect of the extract (100 mg/Kg orally) on Histamine and Bradykinin induced Oedema.

| Treatment | N | +30 | Oedema + +60 | SEM (1%) +120 | +180 min. |
|---|---|---|---|---|---|
| Histamine | 6 | 19.0 ± 0.3 | 43.8 ± 0.3 | 53.3 ± 0.6 | 55.2 ± 0.9 |
| Histamine + Extract | 6 | 6.1 ± 11.0* | 9.9 ± 1.1* | 22.1 ± 1.2* | 35.9 ± 0.6 |
| Bradykinin | 6 | 14.3 ± 0.6 | 19.3 ± 0.8 | 29.4 ± 0.4 | 47.0 ± 0.6 |
| Bradykinin + Extract | 6 | 13.1 ± 0.7 | 14.0 ± 1.3 | 29.0 ± 0.9 | 36.5 ± 0.4 |

Significance relative to the respective control group data * p < 0.001.

TOPICAL ANTIINFLAMMATORY ACTIVITY:

Carrageenan-induced Pedal Oedema Test:

Dose dependent antiinflammatory response was observed with the standardized extract (b=0.0287, r=0.991, p<0.001 with $ED_{50}$ value=9.6 % (95% CL=8.56–10.72) as well as with the mixture of Apigenin glycoside & Luteolin glycoside (4:1) (b=0.0169, r=0.989, p<0.001) with $ED_{50}$ value= 1.12% (95% CL=0.045–2.195) when calculated with +180 min data on topical application, in the carrageen-induced foot paw oedema in mice.

It is thus concluded that the standardized extract is an antiinflammatory agent against two models of acute inflammatory reaction but appears to be relatively less potent than Indomethacin given by a different route (i.p.).

TABLE 1

Modification of Carrageenan-induced Pedal Oedema in Rats following oral Administration of the extract and Intraperitoneal treatment with Indomethacin.

|  | Dose mg/Kg | N | +30 | Oedema + +60 | SEM (%) +120 | +180 min. |
|---|---|---|---|---|---|---|
| The Standardized | 50 | 6 | 8.5 ± 2.8 | 23.9 ± 1.7 | 37.7 ± 5.7 | 48.5 ± 5.0** |
| Extract | 100 | 6 | 3.1 ± 1.4* | 9.2 ± 1.8*** | 25.4 ± 2.0*** | 36.2 ± 0.9*** |
|  | 200 | 6 | 0.7 ± 4.5** | 1.4 ± 4.7*** | 13.6 ± 7.5*** | 15.0 ± 9.9*** |
| Indomethacin | 0.5 | 6 | 13.6 ± 4.0 | 18.9 ± 4.0 | 28.8 ± 4.2 | ND |
|  | 1.0 | 6 | 9.3 ± 2.3 | 12.3 ± 2.2 | 16.4 ± 1.6 | ND |
|  | 2.0 | 6 | 8.2 ± 1.5 | 12.8 ± 1.8 | 11..8 ± 1.8 | ND |
| Control | — | 22 | 13.0 ± 2.7 | 23.3 ± 3.0 | 51.5 ± 4.6 | 62.7 ± 2.9 |

Significance relative to the respective control.
Group data: *P < 0.01; P < 0.05; *P < 0.001    ND = Not Determined

TABLE 3

Modification of Carrageenan-induced Mice Paw Oedema following Topical Application of the Standardized Extract and Indomethacin.

| Treatment | Dose (%) | N | +60 | +120 | +180 | +240 | +360 | +480 m |
|---|---|---|---|---|---|---|---|---|
| The Standardized Extract | 0.5 | 6 | — | 2.0 | 4.8 | 5.4** | 1.9 | 2.3 |
| | 1.0 | 6 | 12.1** | 16.0* | 17.7 | 10.9* | 3.8 | 2.3 |
| | 2.0 | 6 | 9.1 | 16.0* | 24.2* | 18.2* | 7.7 | 4.6 |
| | 4.0 | 6 | | | | | | |
| | 0.25 | 6 | 24.2** | 26.0* | 37.1*** | 29.1* | 7.7** | 6.9 |
| | 0.50 | 6 | 10.6** | 9.0* | 12.3*** | 8.9* | 5.2* | 7.9 |
| | 1.00 | 6 | 27.2** | 26.0* | 29.0* | 14.5* | 11.5* | 9.3 |
| Indomethacin | 1.00 | 6 | 30.3 | 28.0* | 46.8*** | 21.2* | 11.5* | 13.9 |
| | 2.00 | 6 | 18.2** | 24.0** | 29.0** | 21.2** | 9.6** | 4.6 |
| | | | 24.2* | 26.0* | 41.9*** | 36.4* | 11.5* | 10.6 |

Significance reletive to the respective control group data: *$p < 0.01$   $p < 0.05$   *$p < 0.001$ The duration of action of topical preparation was determined by studying the effects of different concentrations of the drug on oedema over a period of 8 hr. As evident from the Table 3, the peak inhibition was observed after 3–4 hours of carrageenan injection beginning at 2 hr for the extract at lower concentrations (0.5–2.0%) and 1 hr. at 4% concentration. A similar kinetic response was observed for the mixture of Apigenin glycoside & luteolin glycoside (4:1) (0.2–1%) and lndomethacin (1–2%). The maximal effect of the mixture of apigenin glycoside and luteolin glycoside preparations observed at 4% concentration (37.1% inhibition) and 1% concentration (46.8% inhibition), respectively, was comparable to that of indomethacin at 2 percent concentration (41.9% inhibition).

The topical effects of indomethacin were comparable with published results of mice carragenan-induced paw oedema (Schrier, D. J., Moniot, S., Gluckman, M. I. and Gilberston, R. B., J. Pharm. Pharmacol., 39, 57,1989).

The mixture of apigenin glycoside & luteolin glycoside was found to possess significant AIA on oral administration with $ED_{50}$ value=5.98 mg/kg (1.12%) to carageenan-induced paw oedema in rats which is comparable to $ED_{50}$ value=1.11% obtained on evaluation of topical AIA data of same fraction, suggesting that this mixture of compounds has both topical as well as oral AIA. The oral absorption of drug as a result of preening may also be considered in topical effect. However, percutaneous absorption of apigenin glycoside has also been reported. When compared to indomethacin this fraction demonstrated a greater antiinflammatory action and slightly higher inhibition of the later phases of oedema. This is attributed to the activity of luteolin glycoside present in the fraction which is reported to decrease swelling in the later phase of oedematus reaction while apigenin glycoside acts in the earlier phase. Hence it is concluded that the standardized extract and the mixture of apigenin glycoside & luteolin glycoside have significant AIA Further, comparable $ED_{50}$ values of topical and oral administration of the standardized extract suggest that the topical effect appears to be independent of systemic absorption.

Croton Oil Ear Test:

The test used was described in published literature, where apigenin 7-glucoside was used as a reference sample. Luteolin glycoside (300 μg/ear) significantly inhibited the croton-oil induced (72%) and showed a dose dependent inhibition of the oedematous response to croton oil. The activity of the compound is comparable to that of apigenin 7-glucoside. Since the standardized extract also contain similar glycosides, hence also active, but to a lesser extent than the mixture of apigenin glycoside & luteolin glycoside. From this data it can be concluded that these glycosides possess an AIA similar to that already described for other chemically related glycosides.

This comparative study of the standardized extract, apigenin glycoside, luteolin glycoside, and the mixture of apigenin glycoside & luteolin glycoside was confirmed independently by a Pharmacology Institute in Italy on the instruction of the inventors. The data on croton oil ear test in mice was found in agreement with data obtained in our laboratory using carrageenan model; any difference in the responses was attributed to the different administration routes.

Some of the results obtained by Italian Institute are reproduced below (Table 4). Indomethacin and hydrocortisone were used as the reference drugs.

TABLE 4

Anti inflammatory activity of the products tested.

| Products | $ID_{50}$ μg/ear | Activity Ratio[a] μmol/ear | on Molar basis |
|---|---|---|---|
| Indomethacin | 46.1 | 0.126 | 1.00 |
| Hydrocortisone | 3.3 | 0.009 | 14.00 |
| Apigenin glycoside* | 29.8 | 0.110 | 1.18 |
| Luteolin glycoside* | 38.4 | 0.135 | 0.96 |
| Quercetin* | 60.3 | 0.200 | 0.65 |
| Apigenin-7-glucoside | 175 | 0.404 | 0.32 |
| Rutin | 282 | 0.462 | 0.28 |

[a]Indomethacin = 1
*Main constiuents of the standardized extract.

Apigenin glycoside and luteolin glycoside appear to be the most active compounds among the compounds tested and are similar in potency to indomethacin, whereas other glycosides are less active. The potency of aglycones has been shown to be strictly propotional to their polarity (data not shown) suggesting that the percutaneous absorption may be an activity-limiting factor.

Study on Duration of Topical AIA Constituents of the Extract:

The effect of apigenin glycoside and luteolin glycoside has been further investigated for the AIA, beyond the standard time of 6 hours; this activity was assessed as oedema (Table 5) and Leucocyte infiltrate inhibition (Table 6) at doses that normally produce an almost complete inhibition of oedema 6 hours after treatment.

TABLE 5

Effect on Oedema Development

| Treatment | Hours after treatment | | |
|---|---|---|---|
| | 6 | 18 | 30 |
| Controls | 7.6 ± 0.4 | 3.7 ± 0.7 | 0.9 ± 0.3 |
| Apigenin (0.037 μMol) glycoside | 0.0 ± 0.1 | 4.5 ± 0.4 | 0.5 ± 0.1 |
| Luteolin (0.27 μMol) glycoside | 2.0 ± 0.5 | 2.2 ± 0.2 | 0.8 ± 0.2 |
| Indomethacin (1.26 μMol) | 0.0 ± 0.1 | 3.1 ± 0.4 | 0.5 ± 0.1 |
| Hydrocortisone (0.41 μMol) | 0.5 ± 0.2 | 0.7 ± 0.1 | 0.7 ± 0.1 |

Data in mg, means ± s.e.; $p < 0.05$

TABLE 6

Effect on granulocyte infiltration (MPO activity).

| Treatment | Hours after treatment | | |
|---|---|---|---|
| | 6 | 18 | 30 |
| Controls | 18.5 ± 2.4 | 38.3 ± 4.8 | 22.8 ± 7.5 |
| Apigenin (0.37 μMol) glycoside | 0.2 ± 0.1 | 8.7 ± 0.5 | 0.9 ± 1.4 |
| Luteolin (0.27 μMol) glycoside | 2.2 ± 0.8 | 13.9 ± 1.5 | 12.0 ± 1.4 |
| Indomethacin (1.26 μMol) | 0.0 ± 0.1 | 10.0 ± 1.6 | 6.8 ± 3.4 |
| Hydrocortisone (0.41 μMol) | 0.0 ± 0.2 | 6.9 ± 2.1 | 8.2 ± 2.4 |

One unit = 1 nMol/min. of tetraguaiacol formed at 25° C. $p < 0.05$

Apigenin glycoside and indomethacin lose their antiinflammatory activity 18 hours after treatment, whereas, at that time, hydrocortisone and luteolin glycoside maintain their effect to a certain extent. The inflammation appears to naturally suppress after 30 hours. The four compounds strongly and permanently inhibit the leukocyte infilteration, measured as myeloperoxidase activity.

Percutaneous Absorption of Topically Active Flavonoids:

The topical AIA of apigenin glycoside, one of the main constituents of the standardized extract, appears to be more potent than Indomethacin. These findings are at variance with the common opinion that such chemical compounds are scantily absorbed through the intact skin. The percutaneous absorption of apigenin glycoside was studied in the same test conditions as used for the assessment of its AIA (inhibition of the croton oil-induced oedema in mice ears). To this purpose two doses of $^3$H-apigenin glycoside (60 and 6 μg/ear) were applied to the inner surface of the mice ears, with or without the usual amount of irritant (35 μg/ear). The specific activity of the labeled compounds was adjusted such that constant amount of radio activity and the amount of radio activity present in the wash solutions after exhaustive washings of the ears at the given times.

The experiment shows first order absorption kinetics. The higher dose of apigenin glycoside is absorbed less rapidly ($t_{1/2}$=4.4 h) than the lower one ($t_{1/2}$=3.4 h). The presence of corton oil enhances the absorpotion of the compound and the absorption rate becomes identical for both the doses ($t_{1/2}$= 2.5 h).

The higher dose of apigenin glycoside almost completely inhibits the oedematous response to croton oil at least within the first 6 hours, whereas the lower dose has no effect on the development of the inflammatory response. Consequently, the enhanced absorption caused by the croton oil is not bound up with an increased permeability of the inflammed skin. The observed effect is probably due to the lipophilic properties of croton oil, which merely acts as vehicle. It can, therefore, be concluded that apigenin glycoside is absorbed through the intact skin and that its absorption-rate may be increased by a suitable pharmaceutical formulation.

MECHANISM OF AIA OF THE EXTRACT:

Flavonoids offer the advantage of high margin of safety and lack the side effects such as ulcerogenicity over the classical antiinflammatory drugs (Agarwal, O. P., Agents Actions, 12, 298, 1982; Havsteen, B., Biochem. Pharmacol., 32, 1141, 1983, Chemical Abstracts: 97 849466). Different approaches to study the antiinflammatory potential of the flavonoids have been made in recent years (Gabor, M., In "Handbook of Experimental Pharmacology: Antiinflammatory Drugs," J. R. Vane, S. H. Ferreira (Eds.) Springer, N.Y., 1979, p.698; Parmar, N. S and Ghosh, M. N., Ind. J. Pharmacol., 10, 277, 1978). It has been suggested that flavonoids not only increase the capillary permeability, they may also inhibit a number of stages in inflammation including granulation, tissue formation and chronic arthritis. The commonly stressed mechanism of action for antiinflammatory drugs is the inhibition of the pathways of arachidonic acid metabolism. However, while this mechanism could apply to luteolin glycoside, apigenin glycoside is unable to affect these processes (published literature) and therefore, other mechanisms of action, such as inhibition of histamine release and radical scavenging activity should be taken into account for this compound. Apigenin and luteolin also decrease leukocyte infiltration and luteolin maintained its effect even after 18 hours of treatment.

Quercetin and its glycosides have been extensively studied for their effects on inflammation and were found to control significantly the exudative and the proliferative phases of the cotton pellet granuloma (Roschin, Yu. V and Geraschenko, G. I., Vopr. Farm. Dolnem Vostoke, 1, 134, 1973; Chem. Abstr., 83,37683, 1975; Kalshinikova, N. A and Geraschenko, G. I., Aktual. Vopr. Farm., 2, 353,1974; Chem. Abstr., 84, 99346, 1976). Quercetin also inhibits mast cell histamine secretion (Benett, J. P., Gomperts, B. D. and Wollenweber, E., Arzneim. Forsch., 31, 433, 1981), neutrophil functions such as release of lysosomal enzymes, oxygen consumption, generation of free radicals and chemotaxis (Busse, W. W., Kipp, D. E and Middleton, E. Jr., J. Allergy Clin. Pharmacol., 73, 801, 1984). Flavonoids are known to inhibit a number of enzymes including cycloxygenase (Sekiya, S. and Okuda, H., Biochem. Biophys. Res. Commun., 105, 1090, 1982). Flavonoids present in *Euphorbia prostrata* were found to be active as oral and topical antiinflammatory agents by the inventors (Singla, A. K. and Pathak, K., J. Ethanopharmacol., 27, 55,1989; Singla, A. K. and Pathak, K., J. Ethanopharmacol., 29, 291, 1990).

EXAMPLES

Process of Manufacture and Evaluation of the Standardized Extract:

The plant *Euphorbia prostrata* was collected by qualified professionals from the hilly regions of Ramgarh in North India. The plant was identified and characterised by the guidelines of WHO (WHO/TRM/91.4, Programme Traditional Medicines World Health Organization Geneva, 1991) and the plant was dried under controlled conditions of temperature and humidity. The whole plant was ground to fine/coarse powder.

The powdered drug (5kg) was packed in a S.S. percolator. The extraction was affected by carrying out cold percolation with 15 lt. of Ethyl Alcohol first time. 10 lt. of menstruum was withdrawn and an equal volume was replaced with fresh ethyl alcohol. The process was repeated 5 times till the drug was exhausted. The alcoholic extracts were combined and concentrated under vacuum at 60° C. The concentrated extract was treated with hot water (80°–90° C.) and water soluble extract was obtained for the flavonoidal components. The aqueous extract was extracted with 5–10 volumes of a non polar organic solvent. The organic phase was dehydrated with suitable desicants and concentrated under vacuum at 60° C. The concentrated extract was dried completely for several hours at 60° C. under vacuum. The purified powdered extract was standardised before proceeding further.

The extract of *Euphorbia prostrata* was characterised by High Performance Liquid Chromatography (HPLC). The HPLC was performed under following conditions and using Waters system equipped with M510 pumps and data station with Millenium software.

Mobile phase: Acetonitrile: 2% acetic acid (17:23)

Column: $C_{18}$ (25OX4 mm/5 $\mu$)

Flow Rate: 1 ml/min

Detector: UV absorbance at 350 nm

The HPLC graph showed five peaks corresponding to the flavonoid components luteolin, 6-methoxy-quercetin glycoside, quercetin, luteolin glycoside and apigenin glycoside. Out of this the major peaks corresponded to luteolin and quercetin (these were confirmed by comparison with authentic luteolin and quercetin samples. Apigenin glycoside and luteolin glycoside were used as the chemical and pharmacological marker for standardisation of the product.

Method of Preparation of Capsules:

Based on the pharmacological studies it was established that each capsule should contain 15–50 mg of Euphorbia extract with HPLC finger printing compounds. Compound a 35% compounds B 9%, rest 6% and total flavonoid content 50%.

Hence, the Euphorbia extract used for each batch was characterised and quantified with respect to flavonoid contents as above. Based on the exact values obtained, the extract quantity of Euphorbia extract per capsules was derived. A typical example of the formula based on average values of flavonoids is as follows:

EXAMPLE 1

|  | For 1 capsule | For 10,000 capsules |
|---|---|---|
| Extract | 15 mg | 0.15 Kg |
| Lactose IP/USP | 250 mg | 2.50 Kg |
| Colloidal Silicone dioxide | 10 mg | 0.10 Kg |
| P. talc | 25 mg | 0.25 Kg |

EXAMPLE 2

|  | For 1 capsule | For 10,000 capsules |
|---|---|---|
| Extract | 15 mg | 0.15 Kg |
| Dibasic Calcium Phosphate | 100 mg | 1.00 Kg |
| Microcrystalline Cellulose | 120 mg | 1.20 Kg |
| Starch (maize) | 60 mg | 0.60 Kg |
| Magnesium stearate | 5 mg | 0.05 Kg |

EXAMPLE 3

|  | For 1 capsule | For 10,000 capsules |
|---|---|---|
| Extract | 15 mg | 0.15 Kg |
| Microcrystalline cellulose | 111 mg | 1.11 Kg |
| Colloidal Silicone dioxide | 3 mg | 0.03 Kg |
| Purified talc | 3 mg | 0.03 Kg |
| Magnesium stearate | 3 mg | 0.03 Kg |

The standardized extract is dissolved in Ethyl Alcohol. Lactose, Colloidal Silicone Dioxide and P. Talc are passed through fine sieves individually. The solution of standardized extract in Ethyl Alcohol is absorbed on lactose and mixed well to achieve uniformity The material is dried at temperature of 60°–70° C. till completely dried. The colloidal silicone dioxide and P.Talc are blended as lubricants. The blend is then analysed for flavonoid contents by HPLC. Based on the assay values the powder is filled in empty hard gelatin capsules at an average fill weight of 300 mg±10 mg. The filled capsules are sealed in air-tight unit packages after Q. C. testing.

Method of Preparation of Ointment:

The standardized extract used for preparation of ointment was characterised in a similar manner as described in the preparation of capsules. Based on the exact values obtained, the exact percentage of standardized extract in ointment was derived. A typical example of the formula based on average values of flavonoids is as follows.

EXAMPLE 4

| Extract | 1% |
|---|---|
| Cetyl alcohol | 20% |
| Beeswax | 24% |
| Glycerin | 12% |
| Sodium lauryl sulphate | 1% |
| Propyl paraben | 0.01% |
| Methyl paraben | 0.03% |
| Purified water | q.s 100% |

EXAMPLE 5
Hydrophilic Ointment

| Extract | 1% |
|---|---|
| Methyl paraben | 0.026% |
| Propyl paraben | 0.015% |
| Sodium lauryl sulphate | 1% |
| Propylene glycol | 12% |
| Stearyl alcohol | 25% |
| White petrolatum | 25% |
| Purified water | q.s 100% |

EXAMPLE 6
Polyethylene Glycol Ointment

| Extract | 3% |
|---|---|
| Polyethylene glycol 3350 | 40% |
| Polyethylene glycol 400 | 57% |

The standardized extract is dissolved in glycerin and a small portion of purified water. Sodium lauryl sulphate, methyl paraben and propyl paraben are incorporated in the solution. The solution is warmed to 65°–75° C. Simultaneously, cetyl alcohol and beeswax are molten at about 75° C. The aqueous phase is added slowly to the oily phase under constant stirring and keeping the temperature between 65° C. to 75° C. The resultant emulsion is stirred further for 1 hour and the weight is made up to 100% with warm purified water, if required. The ointment is allowed to cool and de-aerated. The final product is subjected to quality control testing and filled into lacquered aluminum collapsible tubes and sealed.

EVALUATION OF CLINICAL EFFICACY OF CAPSULES AND OINTMENT

The clinical evaluation of the pharmaceutical composition of this invention was done by University Institute of Pharmaceutical Sciences with the help of the University Health Centre, Punjab University, Chandigarh. After assessing the antiinflammatory action and toxicity testing in animals and based on the safe use of plant in Indian Traditional Medicine for other conditions, the drug was administered in oral dosage form and topical application to patients with complaints of hemorrhoids and fissures. Majority of the patients either did not respond or had relapse with other forms of therapy. Patients were normally given one/two capsules a day for a period of 3–9 days. Some patients received both oral and topical preparation. Approximately 32,000 patients had been administered the drug. Most of the patients responded to one course of treatment without any side effects.

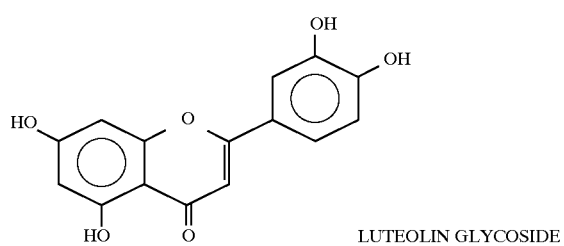
LUTEOLIN GLYCOSIDE

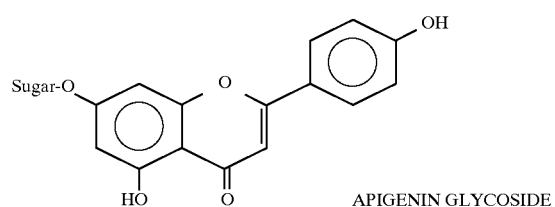
APIGENIN GLYCOSIDE

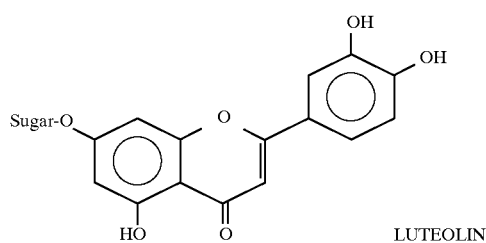
LUTEOLIN

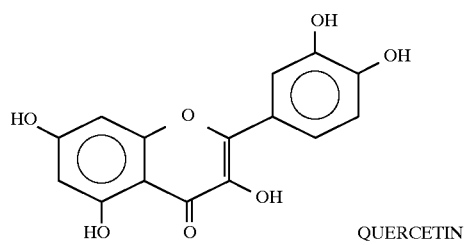
QUERCETIN

-continued

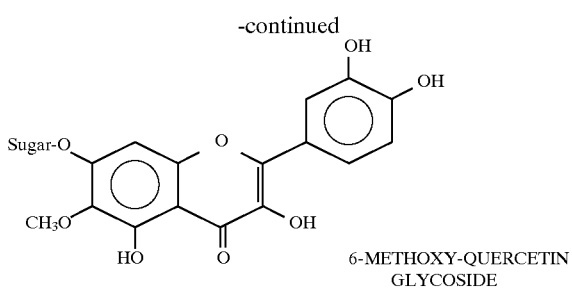
6-METHOXY-QUERCETIN GLYCOSIDE

Chemical Structures of five flavonoid compounds of the standardised extract of *Euphorbia prostrata*

We claim:

1. A pharmaceutical composition for the treatment of anorectal and colonic diseases comprising a pharmaceutically acceptable base and an effective amount of a flavanoid containing extract from the plant *Euphorbia prostate*
wherein the flavanoid is about 35 to 62% by weight of the extract, wherein the flavanoid is apigenin-7-glycoside, luteolin-7-glycoside, 6-methoxy quercetin 3 glycoside, quercetin and luteolin, wherein apigenin-7-glycoside is about 30–45% by weight of the extract, luteolin-7-glycoside is about 3–9% by weight of the extract, and 6-methoxy quercetin 3 glycoside is about 1 to 6% by weight of the extract, quercetin is about 1 to 2% by weight of the extract, and luteolin is about 1 to 2% by weight of the extract.

2. A composition as claimed in claim 1, wherein the anorectal disease is hemorrhoids, fissures, cracks, fistulas, abscesses, inflammatory bowel disease, ulcerative colitis, or Crohns disease.

3. A composition as claimed in claim 1 further comprising tannins at about 5% by weight of the extract, resins, gums at about 10 to 15% by weight of the extract, pigments, sterols, or triterpenoids.

4. A composition as claimed in claim 1 comprising an additional therapeutic agent.

5. A composition as claimed in claim 4 wherein the therapeutic agent is an astringent, an anesthetic, an anesthetic salt, an anesthetic in combination with an anesthetic salt, a vasoconstrictor, a protectant, a counterirritant, a keratolytic, an anti-cholinergic, a wound healing agent or an anti-microbial agent.

6. A composition as claimed in claim 5, wherein the therapeutic agent is an astringent.

7. A composition as claimed in claim 6, wherein the astringent is selected from the group consisting of calamine, zinc oxide, hamamelis water, bismuthresorcinol compound, bismuth subgallate, peruvian balsam, aluminum chlorhyudroxy allantoinate and tannic acid.

8. A composition as claimed in claim 6 wherein the amount of the astringent is about 0.2% to 60% by weight.

9. A composition as claimed in claim 5, wherein the therapeutic agent is selected from an anesthetic, an anesthetic salt, or an anesthetic in combination with an anesthetic salt.

10. A composition as claimed in claim 9, wherein the therapeutic agent is selected from the group consisting of benzocaine, diperodon, pramoxine, camphor, dibucaine, phenol, tetracaine, and phenacaine.

11. A composition as claimed in claim 9 wherein the anesthetic is about 0.25% to 25% by weight.

12. A composition as claimed in claim 5, wherein the therapeutic agent is a vasoconstrictor.

13. A composition as claimed in claim 12, wherein the vasoconstrictor is selected from ephedrine, phenylephrine, or phenylephrine in combination with a phenylephrine salt.

14. A composition as claimed in claim 5, wherein the therapeutic agent is a counterirritant.

15. A composition as claimed in claim 14, wherein the counterirritant is menthol and is about 0.25 to 2.5% by weight.

16. A composition as claimed in claim 5, wherein the therapeutic agent is a protectant.

17. A composition as claimed in claim 16, wherein the protectant is selected from the group consisting of aluminum hydroxide gel, calamine, cocoa butter, cod oil, shark liver oil, starch, white petrolatum, wool alcohol, zinc oxide, vegetable oil, castor oil, polyethylene glycol, and propylene glycol.

18. A composition as claimed in claim 16 wherein the protectant is about 5.0% to 88.0% by weight.

19. A composition as claimed in claim 5, wherein the therapeutic agent is a wound healing agent.

20. A composition as claimed in claim 19, wherein the wound healing agent is selected from vitamin A, vitamin D, Peruvian balsam, cod liver oil and live yeast cell derivatives.

21. A composition as claimed in claim 19 wherein the vitamin A and the vitamin D are about 0.005% to 0.04% by weight, said Peruvian balsam is about 0.5% to 2.5% by weight, cod liver oil is about 1.0% to 6.0% by weight and live yeast cell derivatives are about 2 to 50,000 units per gram.

22. A composition as claimed in claim 5, wherein the therapeutic agent is an antimicrobial agent.

23. A composition as claimed in claim 22, wherein the antimicrobial agent is selected from the group consisting of benzethonium chloride, benalkonium chloride, phenol, menthol, chlorothymol, camphor and 8-hydroxyquinoline sulfate.

24. A composition as claimed in claim 22, wherein the antimicrobial agent is about 0.02% to 40% by weight.

25. A composition as claimed in claim 5, wherein the therapeutic agent is a keratolytic.

26. A composition as claimed in claim 25, wherein the keratolytic is selected from aluminum chlorhydroxy allanoinate and resorcinol.

27. A composition as claimed in claim 25 wherein the keratolytic is about 0.2% to 3.5% by weight.

28. A composition as claimed in claim 5, wherein the therapeutic agent is an anticholinergic.

29. A composition as claimed in claim 28, wherein the anticholinergic is selected from the group consisting of atropine, a solanaceous alkaloid, and atropine in combination with the solanaceous alkaloid.

30. A composition as claimed in claim 28 wherein the anticholinergic is about 0.2% to 0.1 % by weight.

31. A composition as claimed in claim 1 wherein the composition is in the form of a cream, ointment, solution, spray, foam, suppository, medicated pad, bandage, powder, suspension, film, flake, oral hard gelatin capsule, soft gelatin capsule, coated tablet, uncoated tablet, sustained release dosage form, liquid, lozenge, buccal, wafer, or caplet.

* * * * *